(12) United States Patent
Perry

(10) Patent No.: US 11,207,453 B2
(45) Date of Patent: Dec. 28, 2021

(54) DRUG DIFFUSING PERITONEAL DIALYSIS CATHETER

(71) Applicants: Baxter International Inc., Deerfield, IL (US); Baxter Healthcare SA, Glattpark (CH)

(72) Inventor: Mark Perry, McHenry, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 376 days.

(21) Appl. No.: 16/421,743

(22) Filed: May 24, 2019

(65) Prior Publication Data

US 2020/0368421 A1    Nov. 26, 2020

(51) Int. Cl.
*A61M 1/28* (2006.01)
*A61M 25/02* (2006.01)
*A61M 25/00* (2006.01)

(52) U.S. Cl.
CPC ........... *A61M 1/285* (2013.01); *A61M 1/284* (2014.02); *A61M 25/02* (2013.01); *A61M 1/287* (2013.01); *A61M 25/003* (2013.01); *A61M 25/0029* (2013.01); *A61M 2025/0293* (2013.01)

(58) Field of Classification Search
CPC .. A61M 1/285; A61M 1/284; A61M 25/0029; A61M 25/003
See application file for complete search history.

(56) References Cited

U.S. PATENT DOCUMENTS

| | | |
|---|---|---|
| 3,981,299 A | 9/1976 | Murray |
| 4,755,171 A | 7/1988 | Tennant |
| 5,308,338 A | 5/1994 | Baird |
| 5,772,639 A | 6/1998 | Lampropoulos et al. |
| 5,817,072 A | 10/1998 | Lampropoulos et al. |
| 2007/0161967 A1 | 7/2007 | Fischer et al. |
| 2018/0110962 A1 | 4/2018 | Doshi et al. |
| 2019/0046488 A1* | 2/2019 | Rosenblatt ............ A61K 45/06 |

FOREIGN PATENT DOCUMENTS

EP            0145505           6/1985

* cited by examiner

*Primary Examiner* — Bradley J Osinski
(74) *Attorney, Agent, or Firm* — K&L Gates LLP

(57) ABSTRACT

A peritoneal dialysis catheter includes: a catheter tube defining a lumen for carrying peritoneal dialysis fluid to at least one aperture located at or near a distal end of the lumen; at least one cuff located along the outside of the catheter tube; an access site proximally spaced from the at least one cuff, the access site allowing an antimicrobial agent to be introduced into the catheter tube; a reservoir operable with the catheter tube and in fluid communication with the access site, the reservoir storing an amount of the antimicrobial agent received from the access site after an antimicrobial agent introducer is removed from the access site; and a delivery area of the catheter tube in fluid communication with the reservoir, the delivery area positioned so as to target delivery of the antimicrobial agent to the at least one cuff or other desired location along the catheter tube.

20 Claims, 8 Drawing Sheets

DRUG DIFFUSING PERITONEAL DIALYSIS CATHETER

BACKGROUND

Peritoneal dialysis ("PD") catheters are placed through a patient's skin and abdominal wall to provide regular access for dialysis solution input and effluent drainage. Cuffs may be placed below the epidermis and at the abdominal wall to support tissue attachment. Inflammation and infection may occur at the exit site and along the substrate tunnel. At the exit site, inflammation and infection may present as purulent with or without erythema of the skin at the catheter-epidermis interface. Tunnel infections are usually occult but may present with erythema, edema and tenderness along the subcutaneous tunnel path. *Staph aureus* and *Pseudomonas* exit site infections are often associated with tunnel infections.

Once infection presents with exudate the site has to be cultured and cleared. The exit side is dressed. Culture results dictate the course of antibiotic treatment (intravenous ("IV") or oral ("PO")) and additional topical treatment if needed. If the infection is refractory, repeats due to the same organism, involves tunnel abscess, or is associated with peritonitis, the catheter may have to be removed and the patient may not be able to continue with a PD therapy. The patient may then have to resort to hemodialysis ("HD") or receive a transplant.

A need for an improved PD catheter is needed accordingly.

SUMMARY

The examples described herein disclose multiple embodiments for a drug diffusing peritoneal dialysis ("PD") catheter. In general, the drug diffusing PD catheters of the present invention include a catheter tube. The catheter tube is in various embodiments made of suitable medical grade plastic. Examples of suitable plastics include polyethylene, polypropylene, polystyrene, polyester, polycarbonate, polyvinyl chloride, derivatives and combinations thereof. The catheter tube may alternatively be made of silicone tubing. The catheter tube is sized to be inserted into a patient's peritoneal cavity and defines a lumen for carrying fresh peritoneal dialysis fluid to at least one aperture located at or near a distal end of the lumen for delivery of the fresh peritoneal dialysis fluid into the patient's peritoneal cavity. The at least one aperture and lumen in one embodiment also allow effluent or used peritoneal dialysis fluid to be removed from the patient's peritoneal cavity. In alternative embodiments, the catheter tube defines multiple lumens, for example, a first lumen to introduce fresh PD fluid into the patient's peritoneal cavity and a second lumen to remove effluent PD fluid therefrom.

In an embodiment, at least one cuff is located along the outside of the catheter tube for attaching the catheter tube to the patient. The cuff may be made of any of the materials or combinations discussed above.

The drug diffusing PD catheter includes an access site located at a proximal end of the catheter tube so as to be accessible to a user after the catheter tube is attached to the patient, e.g., via the at least one cuff. The access site is proximally spaced from the at least one cuff along the outside of the catheter. The access site allows the user to inject an antimicrobial agent to into the catheter tube. The access site in an embodiment includes a resealable split septum that repeatedly accepts and seals about an antimicrobial agent introducer, such as a syringe or cannula. The split septum seals itself when the introducer is removed from the access site. The split septum may be made of a softer material, such as silicone.

A reservoir is provided along or within a wall of the catheter tube and is in fluid communication with the access site. The reservoir is configured to store an amount of the antimicrobial agent received from the access site for delivery after the antimicrobial agent introducer is removed from the access site. The reservoir may be disposed annularly about at least a portion of the lumen of the catheter tube. The reservoir is in one embodiment expandable to (i) hold additional antimicrobial agent and (ii) place the additional antimicrobial agent under a slight positive pressure, which helps to move the antimicrobial agent to a desired delivery area of the catheter tube.

The delivery area of the catheter tube may be located distal or adjacent to and in fluid communication with the reservoir. The delivery area is positioned so as to target delivery of the antimicrobial agent to the at least one cuff or exit site, for example. The delivery area is configured to allow the antimicrobial agent to flow through the delivery area to reach the desired delivery area along the catheter tube, e.g., the cuff or exit site. The delivery area in one embodiment is molded to include minute flow paths leading to the at least one cuff. In another embodiment, the delivery area is made of a material that is hydrophilic to the antimicrobial agent, allowing passage of the antimicrobial agent through the delivery area. In a further embodiment, the delivery area is made of a material that allows the antimicrobial agent to diffuse through the delivery area. In any of the above delivery area embodiments, the delivery area may be made of a separate material insert that is fitted to the catheter tube.

In an embodiment in which two or more cuffs are provided (e.g., one for attaching below the epidermis and a second for attaching to the abdominal wall), two or more delivery areas are provided, e.g., one for each cuff, wherein the two or more delivery areas are each in fluid communication with the reservoir. Alternatively, two delivery areas are provided for a single cuff and the exit site, or three delivery areas are provided for two cuffs and the exit site.

In one embodiment, the delivery area is located directly adjacent to the reservoir. Here, the delivery area may provide at least one wall of the reservoir or vice versa. The antimicrobial agent may then flow directly from the reservoir to the delivery area. In another embodiment, the delivery area is located distal from the reservoir (relative to the proximal or outside-the-body end of the catheter). The antimicrobial agent here flows in a flow path leading from the reservoir to the delivery area.

Where two cuffs are provided, for example, the reservoir may be located directly adjacent to the delivery area of the proximal (abdominal) cuff and proximal to the more distal delivery area of the distal (epidermal) cuff. The antimicrobial agent flows directly from the reservoir to the proximal delivery area and through a flow path to the distal delivery area. In an alternative embodiment, the reservoir is located proximal to both proximal and distal cuff delivery areas, such that first and second flow paths lead from the reservoir to the proximal delivery area from the proximal delivery area to the distal delivery area. In yet another embodiment, the reservoir is located between the proximal and distal delivery areas. In still a further alternative embodiment, the reservoir is extended so as to communicate directly with multiple delivery areas, such as proximal and distal cuff delivery areas.

As discussed, the cuffs are not the only desired antimicrobial agent delivery locations along the catheter tube. Delivery areas may also be positioned so as to target delivery of the antimicrobial agent to other or additional desired locations along the catheter, such as the exit site of the catheter tube from the patient, or another subcutaneous area of the catheter tube.

It is contemplated to use the drug diffusing catheters of the present disclosure to deliver the antimicrobial agent to the reservoirs for immediate release in combination with a time-delay release to desired locations along the catheter after installation of the catheter, so as to prevent inflammation and infection. Additionally, antimicrobial agent may be administered periodically after installation and/or when the patient experiences inflammation and infection.

In light of the disclosure herein and without limiting the disclosure in any way, in a first aspect of the present disclosure, which may be combined with any other aspect listed herein unless specified otherwise, a peritoneal dialysis catheter includes (i) a catheter tube sized to be inserted into a patient's peritoneal cavity, the catheter tube defining a lumen for carrying peritoneal dialysis fluid to at least one aperture located at or near a distal end of the lumen for delivery of the peritoneal dialysis fluid into the patient's peritoneal cavity; (ii) at least one cuff located along the catheter tube for attaching the catheter tube to the patient; (iii) an access site proximally spaced from the at least one cuff so as to remain external to the patient when the at least one cuff is attached to the patient, the access site allowing an antimicrobial agent to be introduced into the catheter tube; (iv) a reservoir in fluid communication with the access site, the reservoir configured to store an amount of the antimicrobial agent received from the access site for delivery after an antimicrobial agent introducer is removed from the access site; and (v) a delivery area located distal or adjacent to and in fluid communication with the reservoir, the delivery area positioned so as to target delivery of the antimicrobial agent to the at least one cuff.

In a second aspect of the present disclosure, which may be combined with any other aspect listed herein unless specified otherwise, the at least one cuff includes first and second cuffs, wherein the delivery area of the catheter tube is a first delivery area positioned so as to target delivery of the antimicrobial agent to the first cuff, and which includes a second delivery area positioned so as to target delivery of the antimicrobial agent from the reservoir to the second cuff.

In a third aspect of the present disclosure, which may be combined with the second aspect in combination with any other aspect listed herein unless specified otherwise, the reservoir is in antimicrobial agent flow communication with the first and second delivery areas.

In a fourth aspect of the present disclosure, which may be combined with any other aspect listed herein unless specified otherwise, the access site is configured to seal about the introducer, the introducer including a syringe or cannula.

In a fifth aspect of the present disclosure, which may be combined with any other aspect listed herein unless specified otherwise, the reservoir is an expandable reservoir.

In a sixth aspect of the present disclosure, which may be combined with any other aspect listed herein unless specified otherwise, the reservoir is disposed annularly about at least a portion of the lumen.

In a seventh aspect of the present disclosure, which may be combined with any other aspect listed herein unless specified otherwise, the delivery area is located distal to the reservoir, and wherein the catheter tube defines a flow path leading from the reservoir to the delivery area.

In an eighth aspect of the present disclosure, which may be combined with any other aspect listed herein unless specified otherwise, the delivery area includes first and second delivery areas, and wherein the reservoir is located proximal to the first and second delivery areas or between the first and second delivery areas.

In a ninth aspect of the present disclosure, which may be combined with any other aspect listed herein unless specified otherwise, the delivery area of the catheter tube is at least one of (i) configured to include minute flow paths leading to the at least one cuff, (ii0 hydrophilic to the antimicrobial agent, or (iii) diffusive to the antimicrobial agent.

In a tenth aspect of the present disclosure, which may be combined with any other aspect listed herein unless specified otherwise, a peritoneal dialysis catheter includes (i) a catheter tube sized to be inserted into a patient's peritoneal cavity, the catheter tube defining a lumen for carrying peritoneal dialysis fluid to at least one aperture located at or near a distal end of the lumen for delivery of the peritoneal dialysis fluid into the patient's peritoneal cavity; (ii) an access site located so as to remain external to the patient when the catheter tube is attached to the patient, the access site allowing an antimicrobial agent to be introduced into the catheter tube; (iii) a reservoir in fluid communication with the access site, the reservoir configured to store an amount of the antimicrobial agent received from the access site for delivery after an antimicrobial agent introducer is removed from the access site; and (iv) a delivery area located distal or adjacent to and in fluid communication with the reservoir, the delivery area positioned so as to target delivery of the antimicrobial agent to a desired location along the catheter tube.

In an eleventh aspect of the present disclosure, which may be combined with the tenth aspect in combination with any other aspect listed herein unless specified otherwise, the desired location along the catheter tube includes at least one of (i) a cuff located along the outside of the catheter tube for attaching the catheter tube to the patient, (ii) an exit site of the catheter tube from the patient, or (iii) a subcutaneous area of the catheter tube.

In a twelfth aspect of the present disclosure, which may be combined with the tenth aspect in combination with any other aspect listed herein unless specified otherwise, the delivery area is integrated with a cuff for attaching the catheter tube to the patient.

In a thirteenth aspect of the present disclosure, which may be combined with the tenth aspect in combination with any other aspect listed herein unless specified otherwise, the reservoir is an expandable reservoir.

In a fourteenth aspect of the present disclosure, which may be combined with the tenth aspect in combination with any other aspect listed herein unless specified otherwise, the reservoir is disposed annularly about at least a portion of the lumen.

In a fifteenth aspect of the present disclosure, which may be combined with the tenth aspect in combination with any other aspect listed herein unless specified otherwise, the delivery area is located distal to the reservoir, and wherein the catheter tube defines a flow path leading from the reservoir to the delivery area.

In a sixteenth aspect of the present disclosure, which may be combined with the tenth aspect in combination with any other aspect listed herein unless specified otherwise, the delivery area includes first and second delivery areas, and wherein the reservoir is located proximal to the first and second delivery areas or between the first and second delivery areas.

In a seventeenth aspect of the present disclosure, which may be combined with the tenth aspect in combination with any other aspect listed herein unless specified otherwise, the delivery area of the catheter tube is at least one of (i) configured to include minute flow paths leading to the at least one cuff, (ii) hydrophilic to the antimicrobial agent, or (iii) diffusive to the antimicrobial agent.

In an eighteenth aspect of the present disclosure, which may be combined with any other aspect listed herein unless specified otherwise, a peritoneal dialysis catheter includes (i) a catheter tube sized to be inserted into a patient's peritoneal cavity, the catheter tube defining a lumen for carrying peritoneal dialysis fluid to at least one aperture located at or near a distal end of the lumen for delivery of the peritoneal dialysis fluid into the patient's peritoneal cavity; (ii) an access site located so as to remain external to the patient when the catheter tube is attached to the patient, the access site allowing an antimicrobial agent to be introduced into the catheter tube; (iii) a reservoir in fluid communication with the access site, the reservoir configured to store an amount of the antimicrobial agent received from the access site for delivery after an antimicrobial agent introducer is removed from the access site; (iv) a first delivery area located distal or adjacent to and in fluid communication with the reservoir, the first delivery area positioned so as to target delivery of the antimicrobial agent to a first desired location along the catheter tube; and (v) a second delivery area located distal or adjacent to and in fluid communication with the reservoir, the second delivery area positioned so as to target delivery of the antimicrobial agent to a second desired location along the catheter tube.

In a nineteenth aspect of the present disclosure, which may be combined with the eighteenth aspect in combination with any other aspect listed herein unless specified otherwise, the first delivery area is located adjacent to the reservoir and the second delivery area is located distal to the reservoir, the catheter tube defining a flow path between the first and second delivery areas.

In a twentieth aspect of the present disclosure, which may be combined with the eighteenth aspect in combination with any other aspect listed herein unless specified otherwise, the first delivery area is located distal to the reservoir, the catheter tube defining a first flow path between the reservoir and the first delivery area, and wherein the second delivery area is located distal to the first delivery area, the catheter tube defining a second flow path between the first and second delivery areas.

In a twenty-first aspect of the present disclosure, which may be combined with the eighteenth aspect in combination with any other aspect listed herein unless specified otherwise, the reservoir is extended so as to be adjacent to or include the first and second delivery areas.

In a twenty-second aspect of the present disclosure, which may be combined with the eighteenth aspect in combination with any other aspect listed herein unless specified otherwise, the first and second desired locations along the catheter tube include at least one of (i) a cuff located along the outside of the catheter tube for attaching the catheter tube to the patient, (ii) an exit site of the catheter tube from the patient, or (iii) a subcutaneous area of the catheter tube.

In a twenty-third aspect of the present disclosure, any of the structure and functionality disclosed in connection with FIGS. 1 to 8 may be combined with any of the other structure and functionality disclosed in connection with FIGS. 1 to 8.

In light of the present disclosure and the above aspects, it is therefore an advantage of the present disclosure to provide an improved peritoneal dialysis ("PD") catheter.

It is another advantage of the present disclosure to provide a drug diffusing PD catheter.

It is a further advantage of the present disclosure to provide PD catheter that is useable to prevent infection and to fight existing infection.

It is still another advantage of the present disclosure to provide a drug diffusing PD catheter having a time-delay antimicrobial agent release to desired catheter tube locations.

It is still a further advantage of the present disclosure to provide a drug diffusing PD catheter that is relatively inexpensive to produce.

It is yet another advantage of the present disclosure to provide a drug diffusing PD catheter that is relatively uncomplicated to produce and use.

The advantages discussed herein may be found in one, or some, and perhaps not all of the embodiments disclosed herein. Additional features and advantages are described herein, and will be apparent from, the following Detailed Description and the figures.

DETAILED DESCRIPTION

Figure 1:
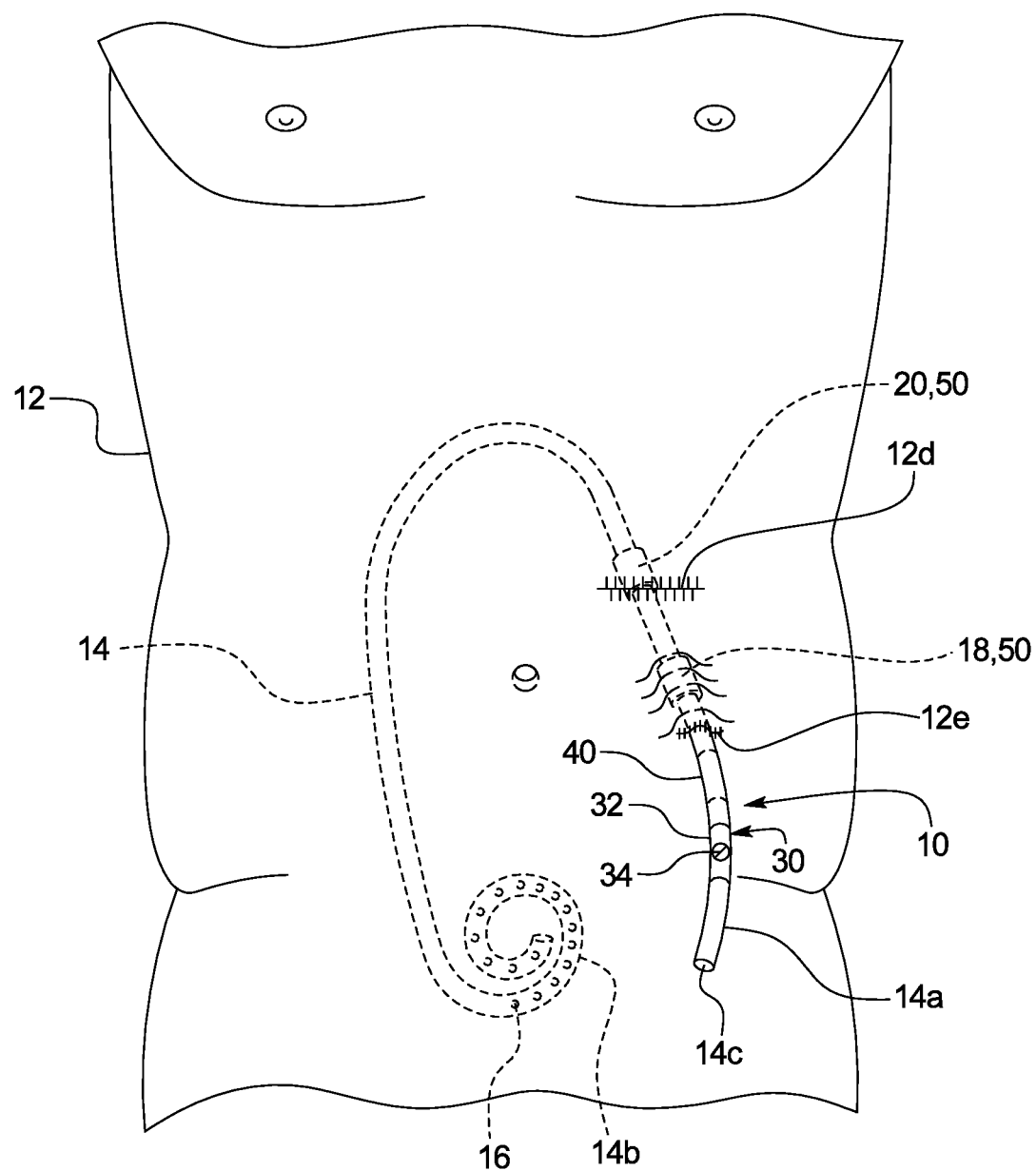
FIG. 1 is a front view of a patient having an installed drug diffusing catheter of the present disclosure.
Figure 2:
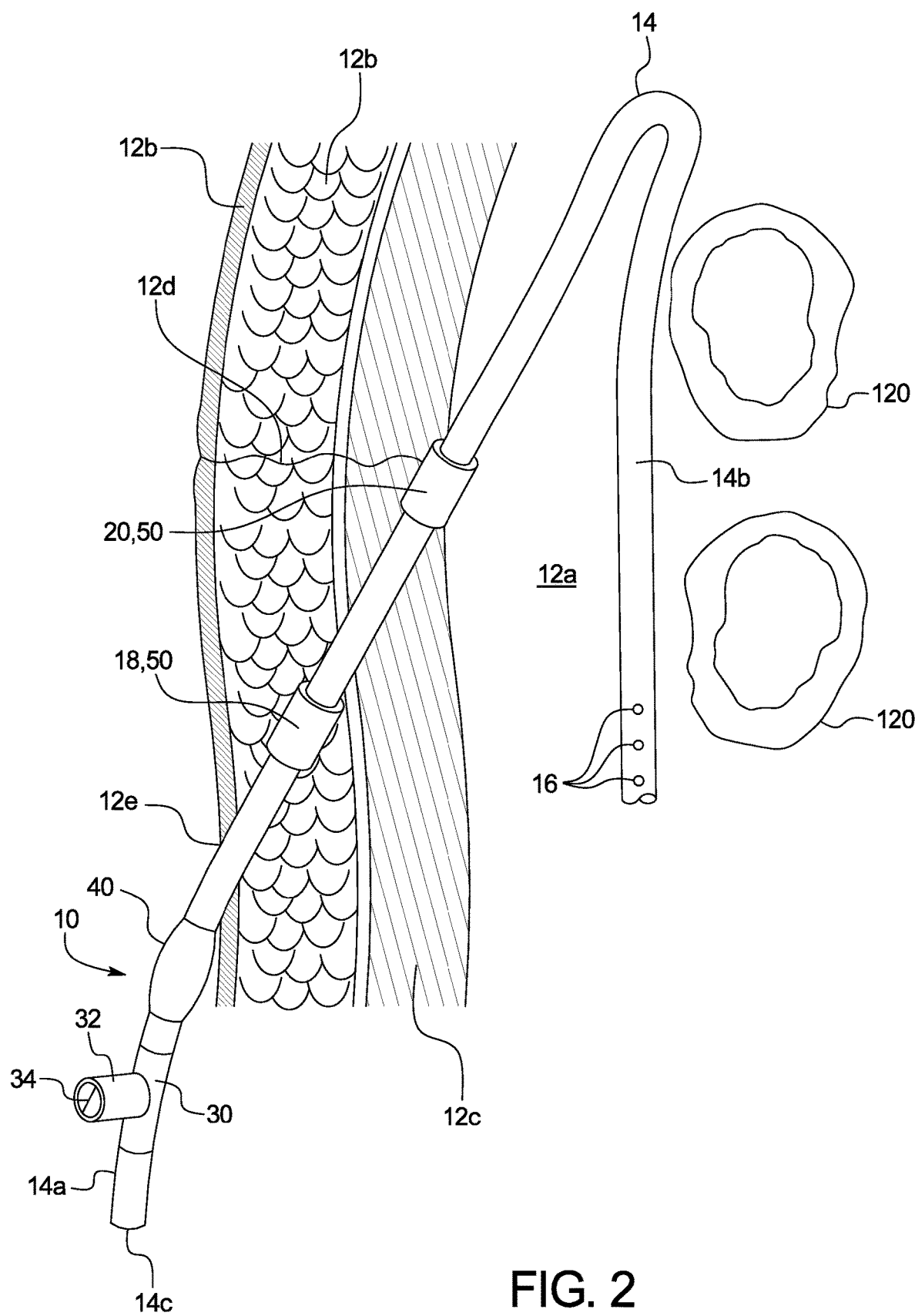
FIG. 2 is a side-sectioned view of a patient having an installed drug diffusing catheter of the present disclosure.

Referring now to FIGS. 1 and 2, one embodiment of a drug diffusing peritoneal dialysis ("PD") catheter 10 of the present disclosure is illustrated installed in patient 12. Catheter 10 includes a catheter tube 14 having a proximal end 14a and a distal end 14b. Proximal end 14a is located outside of patient 12 (solid line), while distal end 14b is shown located inside patient 12 (dashed line). Distal end 14b is illustrated as having multiple apertures or holes 16 allowing fresh PD fluid to be delivered from catheter tube 14 to the peritoneal cavity 12*a* of patient 12 and for removing used PD fluid or effluent from the peritoneal cavity 12*a* of patient 12.

Catheter 10 is illustrated generally as a singler lumen catheter in which the same single lumen is used to deliver fresh PD fluid to patient 12 and to remove effluent PD fluid from patient 12. It should be appreciated however that catheter 10 may alternatively be a multi- or dual lumen catheter in which fresh fluid is delivered through a first lumen of catheter 10 to patient 12 and effluent PD fluid is removed via a second lumen of catheter 10 from patient 12. Three or more lumens may be provided alternatively.

In the illustrated embodiment, catheter tube 14 is attached to patient 12 via first and second cuffs 18 and 20. First or proximal cuff 18 is attached to the patient's abdominal wall 12*b* (including skin and subcutaneous tissue), while second or distal cuff 20 is placed below the patient's epidermis 12*c* via an entrance site 12*d*. Proximal end 14*a* exits patient 12 via exit site 12*e*. Catheter tube 14 and cuffs 18 and 20 in various embodiments are made of a suitable medical grade material, such as silicone or a plastic, such as polyethylene, polypropylene, polystyrene, polyester, polycarbonate, polyvinyl chloride, derivatives and combinations thereof. In an embodiment, implant cuffs 18 and 20 may be polyester felt or other material that allows tissue ingrowth into the cuffs. Subcutaneous tissue grows into the implant cuffs 18 and 20 to anchor the catheter 10 to the patient 12.

A patient transfer set (not illustrated) is connected at proximal tip 14*c* of catheter 14 to perform the prescribed PD modality, such as automated peritoneal dialysis ("APD"), continuous flow peritoneal dialysis ("CFPD"), or continuous ambulatory peritoneal dialysis ("CAPD"). The patient transfer set is closed to prevent contaminants from entering catheter tube 14.

FIGS. 1 and 2 illustrate that proximal end 14*a* of catheter tube 14 includes an access site 30 and an antimicrobial agent reservoir 40 located outside of patient 12 and proximal to exit site 12*e*. Access site 30 as illustrated includes a port 32 that extends in a "T" shaped or 90 degree manner from catheter tube 14. Port 32 alternatively extends at an acute angle, e.g., 30, 45 or 60 degrees from catheter tube 14 and which is angled towards proximal tip 14*c*.

Port 32 in the illustrated includes a resealable split septum 34 that seals around a syringe or cannula or other type of introducer inserted into septum 34 and port 32 to deliver an antimicrobial agent, such as any suitable liquid antibiotic. Split septum 34 may be made of silicone or other softer, compliant material. Access site 30 and antimicrobial agent reservoir 40 are described in more detail below.

Figure 3:
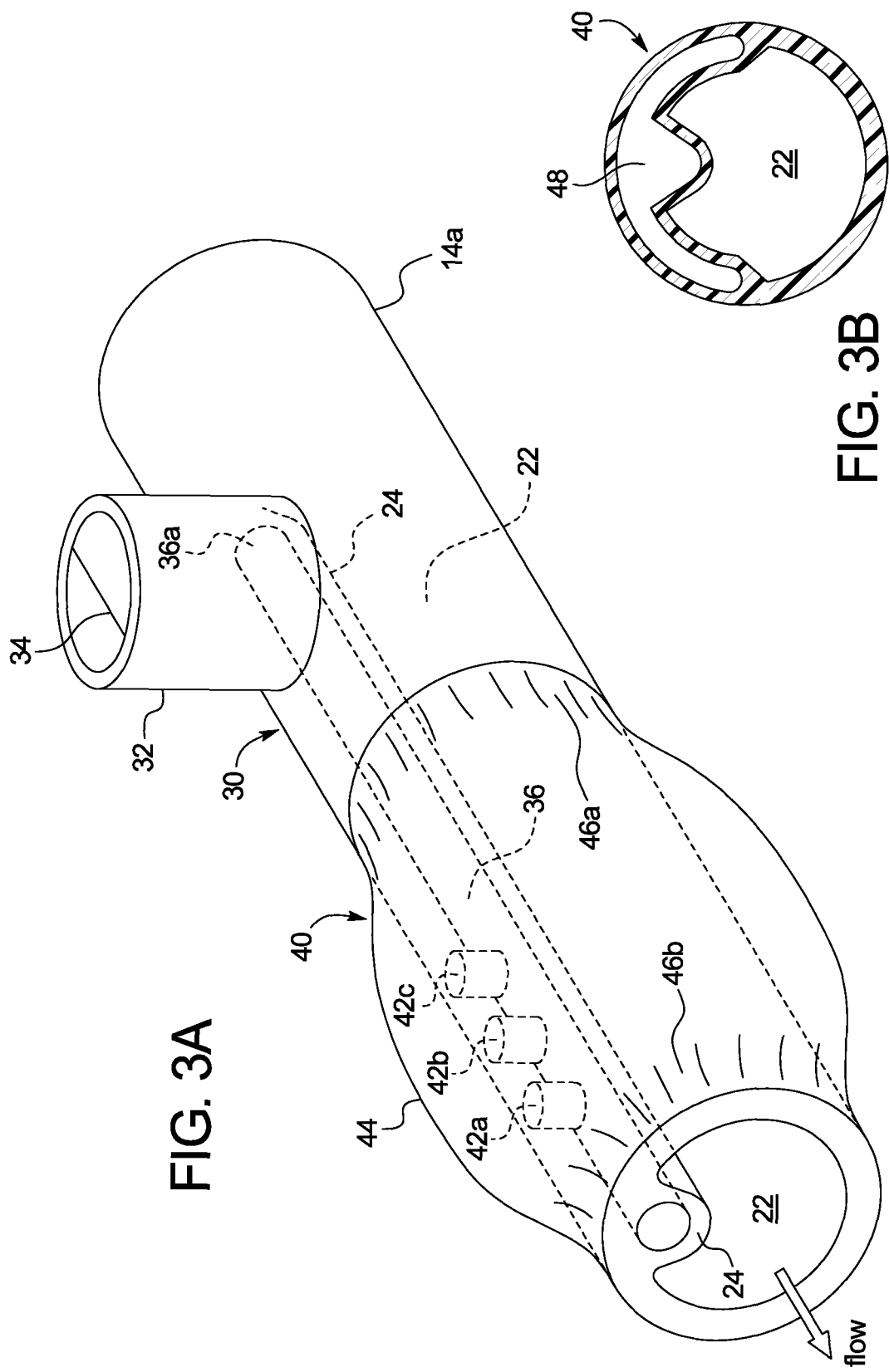
FIG. 3A is a perspective view of a proximal portion of the drug diffusing catheter of the present disclosure illustrating an embodiment of an access site and an antimicrobial agent reservoir.
FIG. 3B is a sectioned elevation view of an alternative antimicrobial agent reservoir of the present disclosure.

Referring now to FIG. 3A, access site 30 and antimicrobial agent reservoir 40 are illustrated in more detail. For ease of illustration, access site 30 and antimicrobial agent reservoir 40 are shown abutting each other. It should be appreciated however that antimicrobial agent reservoir 40 may be spaced away from access site 30 along catheter tube 14. Tube 14 and reservoir 40 as illustrated define a lumen 22 through which fresh and effluent dialysis fluid flows.

Catheter tube 14 and reservoir 14 as illustrated also include a U-shaped radially inward projection 24 that defines an antimicrobial agent flow path 36, which accepts antimicrobial agent from port 32 and resealable split septum 34, and which allows the antimicrobial agent to flow towards the distal end of catheter tube 14. Antimicrobial agent flow path 36 in the illustrated embodiment begins at the center or perhaps slightly on the proximal side of the center of port 32, such that it is easy for the user's introducer (syringe or cannula) to locate flow path 36. To this end, the entrance end 36*a* of flow path 36 may be larger than the diameter of flow path 36 extending through projection 24. The shape and dimensions of projection 24 and the diameter of flow path 36 are selected to (i) interfere with lumen 22 as little as possible and (ii) to allow antimicrobial agent to be flowed through the flow path without undue effort by the user actuating the introducer.

Figure 4:
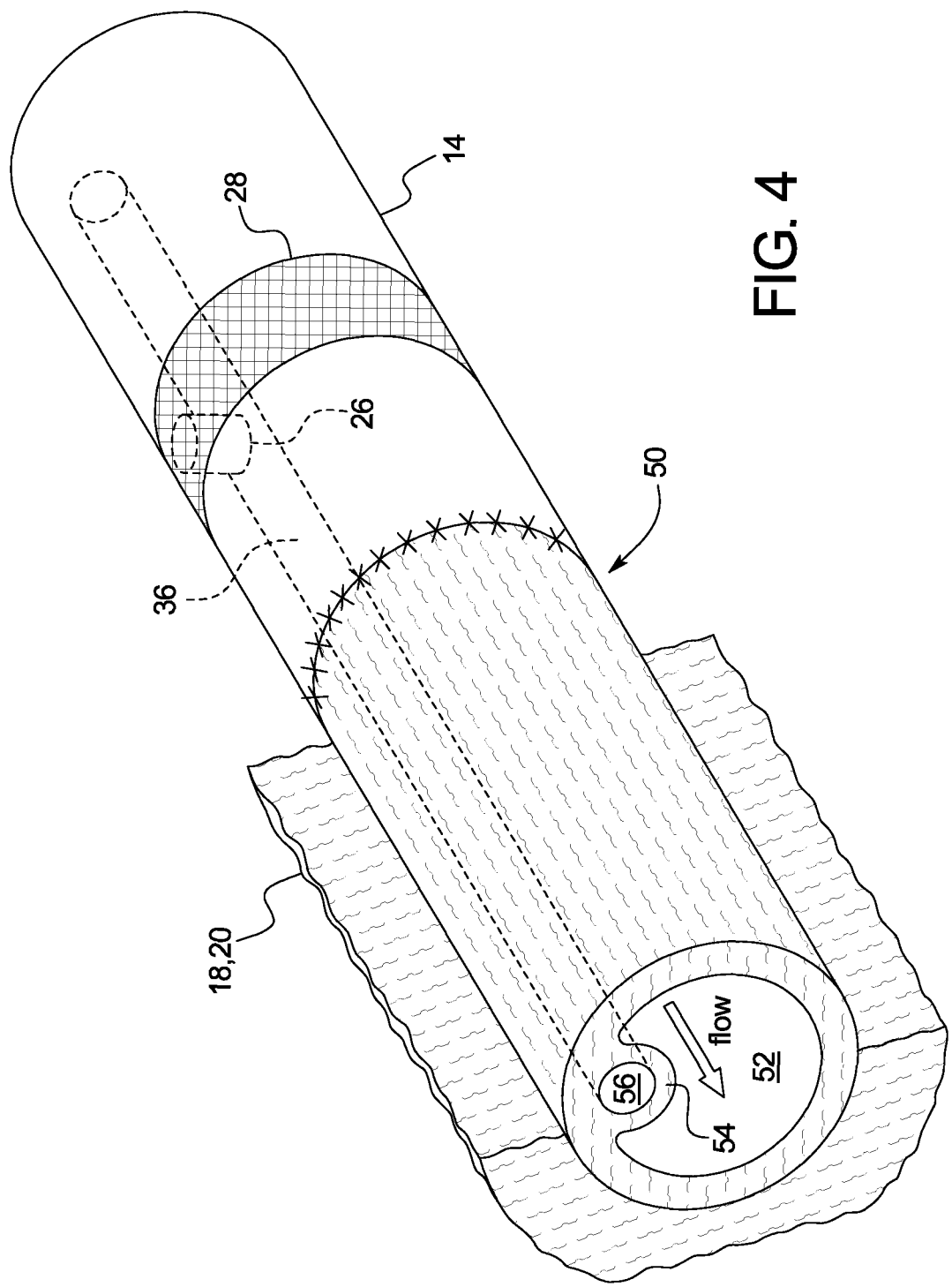
FIG. 4 is a perspective view of a portion of the drug diffusing catheter of the present disclosure illustrating an embodiment of a delivery area for releasing the antimicrobial agent.

Regarding air displaced by the antimicrobial agent, it is contemplated for catheter tube 14 to provide a vent port 26 (FIG. 4) extending outwardly from flow path 36 through the wall of the catheter tube to allow displaced air to be vented to atmosphere. FIG. 4 illustrates that vent port 26 may be covered by a hydrophobic wrap 28, which wraps around catheter tube 14, prevents contaminants from entering flow path 36, and prevents the antimicrobial agent from escaping through vent port 26. Vent port 26 may be located proximal to proximal cuff 18 so that the displaced air is vented outside the body of patient 12. It may be found however that the small amount of air vented is not harmful to patient 12 if vented into patient's epidermis 12*c* on the distal side of distal cuff 20. In one embodiment, vent port 26 is prevented from venting air into the patient's peritoneal cavity 12*a*.

Another method for dealing with air displaced within flow path 36 via the antimicrobial agent is to draw a vacuum on the flow path prior to injecting the antimicrobial agent. The vacuum may be drawn for example by inserting a closed syringe into port 32 via split septum 34 and withdrawing the plunger of the syringe to pull air from flow path 36 into the syringe, creating a vacuum within flow path 36. When the antimicrobial agent is next injected into flow path 36, the vacuum is relieved. Drawing the vacuum as just discussed may be used alternatively or in addition to providing hydrophobic vent port 26 discussed above.

FIG. 3A illustrates an embodiment of antimicrobial agent reservoir 40. Antimicrobial agent reservoir 40 may be located anywhere along catheter tube 14 as discussed in connection with FIGS. 6 to 8. For the ease of illustration, antimicrobial agent reservoir 40 is shown located directly adjacent to access site 30. Antimicrobial agent reservoir 40 is illustrated having multiple ports 42*a* to 42*c* (more or less than three could be provided) that extend from flow path 36 through the wall of catheter/reservoir tube 14. An expandable layer 44 is sealed at proximal and distal ends 46*a* and 46*b* of reservoir 40 to catheter/reservoir tube 14, so as to cover and form an enclosed volume around ports 42*a* to 42*c*. Expandable layer 44 may be sealed at proximal and distal ends 46*a* and 46*b* to catheter tube 14 via thermal sealing, ultrasonic welding, or solvent bonding.

Expandable layer 44 is in one embodiment made of the same material as catheter tube 14, but perhaps in a thinner form. For example, if catheter tube 14 has a wall that is 0.063 inch (1.6 mm) thick, layer 44 may be 0.031 inch (0.79 mm) thick or 0.016 inch (0.40 mm) thick. The thinner thickness of expandable layer 44 allows it to expand and fill with antimicrobial agent. In an alternative embodiment, expandable layer 44 is made of a thinner, film-type, expandable material, such as a latex material, and which is medically safe.

While expandable layer 44 is illustrated in FIG. 3A as being located on the outside of catheter tube 14, layer 44 is provided alternatively on the inside surface of catheter tube 14. Here, ports 42*a* to 42*c* extend instead through the wall of catheter tube 14 into lumen 22. Any of the materials and sealing methods for locating layer 44 on the outside of catheter/reservoir tube 14 are applicable to providing layer 44 on the inside of catheter tube 14. It should also be appreciated that delivering antimicrobial agent is likely performed during a time other than treatment, so that layer 44 expanding within and tending to occlude lumen 22 is not an issue. Once layer 44 deflates and delivers antimicrobial agent to the delivery sites, lumen 22 become fully open.

In still a further alternative embodiment illustrated in FIG. 3B, expandable layer 44 is not provided and instead reservoir 40 is formed as a short section of tubing having a widened flow path 48 that accepts antimicrobial agent from an upstream circular flow path 36 located proxial to and in fluid communication with widened flow path 48 and releases antimicrobial agent to a downstream circular flow path 36 located distal and in fluid communication with widened flow path 48. The short section of tubing forming the alternative version instead reservoir 40 is in one embodiment heat sealed or laser welded to proxial and distal sections of catheter tube 14. Widened flow path 48 may be U-shaped as illustrated and follow the circular outer shape of the reservoir and the circular shape of flow path 36. The thinner walls of the tubing section forming widened flow path 48 allow the walls to be expandable and to perform the function of expandable layer 44.

Reservoir 40 in any of the embodiments described above provides a time-delay release of antimicrobial agent to the desired location(s) along catheter tube 14. When the user inserts the introducer into access site 30 and injects the antimicrobial agent, the antimicrobial agent fills 36 and then builds pressure. Once pressure is built, the antimicrobial agent flows to the delivery area(s) and wets the desired location(s), e.g., cuffs 18 and 20. The backpressure in flow path 36 also fills reservoir 40 until fully expanded. The user removes the introducer from access site 30, leaving reservoir 40 filled. Reservoir 40 deflates over time, providing additional antimicrobial agent to the delivery area(s) and the desired location(s) and maintains a positive pressure on the residual antimicrobial agent within flow path 36, so that it may also be delivered to the delivery area(s) and the desired location(s).

FIG. 4 illustrates an embodiment for delivery area 50. Delivery area 50 is illustrated as being coextensive with cuff 18 or 20 but could alternatively be any desired location(s) along catheter tube 14, e.g., at exit site 12e. In the illustrated embodiment, delivery area 50 has the same cross-sectional shape and size as catheter tube 14, defining a like shaped and sized (i) lumen 52 as lumen 22 of tube 14, (ii) U-shaped radially inward projection 54 as U-shaped gradually inward projection 24 of tube 14 and (iii) flow path lumen 56 as flow path 36 of tube 14. Delivery area 50 in various embodiments is heat sealed or laser welded to proximal and distal ends sections of catheter tube 14.

Delivery area 50 is made of a material that will fluidly spread the antimicrobial agent out within the delivery area prior to it being released to the desired catheter locations, e.g., cuff 18 or 20. The material may be a hydrophilic material (allowing the liquid antimicrobial agent to pass through) or a material that is diffusive to the antimicrobial agent. In a further alternative embodiment, delivery area 50 includes minute flow paths leading from flow path 56 to the outer surface of delivery area 50. In any of these embodiments, antimicrobial agent is allowed to flow from flow path 56 to all parts of the outer surface of delivery area 50 before reaching cuff 18 or 20 and/or exit site 12e.

It is expected that the antimicrobial agent will flow first through the path of least resistance or paths 36 and 56 until reaching an end of the last delivery area 50. Pressure then builds in flow paths 36 and 56 and disperses through the delivery areas 50 as described above prior to reaching the desired catheter locations, e.g., cuffs 18 and 20 and/or exit site 12c.

Cuffs 18 and 20 shown cutaway in FIG. 4 are made of a porous or otherwise non-solid material that allows the patient's abdominal wall 12b to grow into cuff 18 and the patient's epidermis 12c to grow into cuff 20. In an alternative embodiment illustrated in FIG. 5, delivery area 50 is integrated into cuffs 18 and 20 to form a delivery area cuffs 118 and 120. Delivery area cuff 118 would replace dual structures 18 and 50 in FIGS. 1 and 2, while delivery area cuff 120 would replace dual structures 20 and 50. Cuffs 118 and 120 are made of a material that is hydrophilic or diffusive to the antimicrobial agent, and which also allows the patient's abdominal wall 12b to grow into cuff 18 and the patient's epidermis 12c to grow into cuff 20. In an example, cuffs 118 and 120 are made of a hydrophilic polyester felt.

Figure 5:
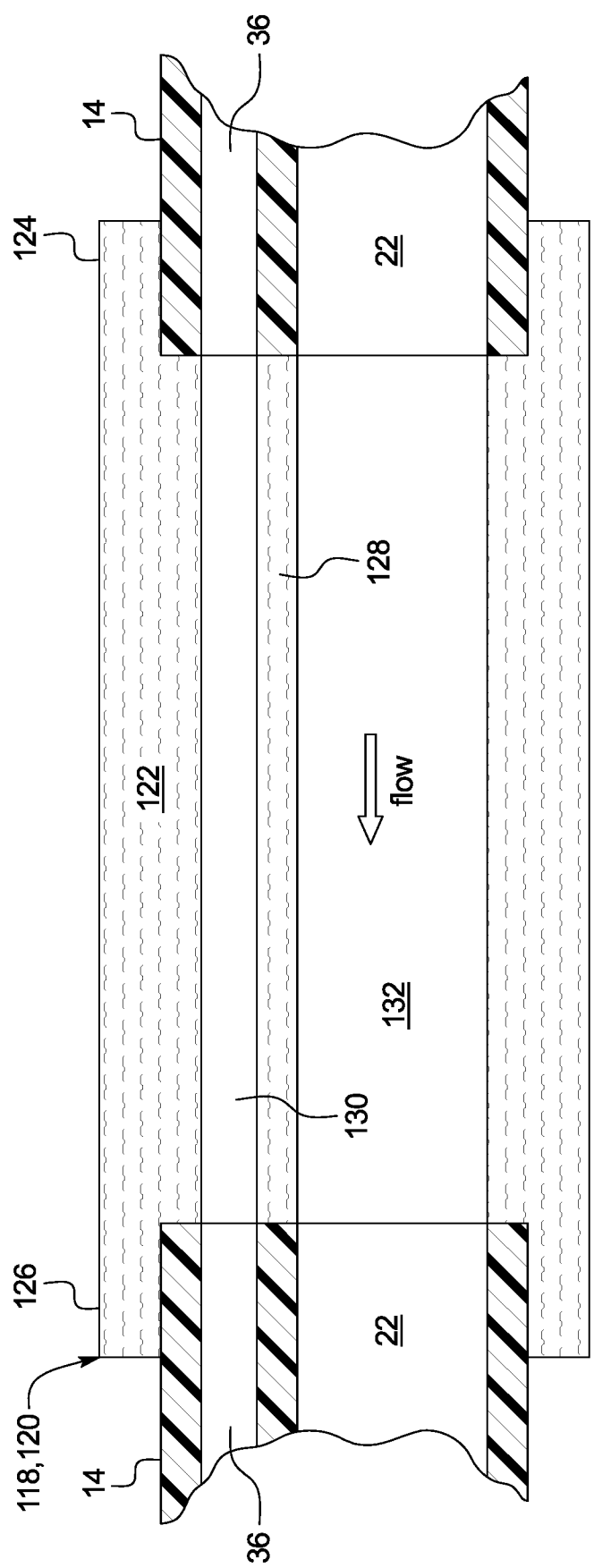
FIG. 5 is a sectioned elevation view of one embodiment of a combined antimicrobial agent delivery area and cuff of the present disclosure.

FIG. 5 illustrates that cuffs 118 and 120 include a body 122 extending to a proximal cap 124 and a distal cap 126, which each accept an end of catheter tube 14 and seal to the catheter tube mechanically, via sonic welding, thermal sealing, solvent bonding or combinations thereof. Body 122 includes a U-shaped radially inward projection 128 that defines a flow path 130, which abuts against and communicates fluidly with flow paths 36 of the sections of catheter tubes 14 that connect to proximal cap 124 and distal cap 126. FIG. 5 also illustrates that peritoneal dialysis fluid lumen 22 of catheter tubes 14 mates with lumen 132 of cuffs 118 and 120. It should be appreciated that (i) the delivery area 50 of FIG. 4 could also have caps, such as proximal cap 124 and distal cap 126, and seal to catheter tubes 14 instead in the manner shown in FIG. 5, and (ii) the integrated delivery area cuffs 118 and 120 of FIG. 5 do not have to have caps 124 and 126 and may seal to catheter tubes 14 instead in the manner shown in FIG. 4.

Although not illustrated, integrated delivery areas and cuff 118 and 120 may be further integrated to include the reservoir-forming, u-shaped opening 48 of FIG. 3B. In this manner, reservoir 40 may extend to and include one or more delivery area.

Figure 6:
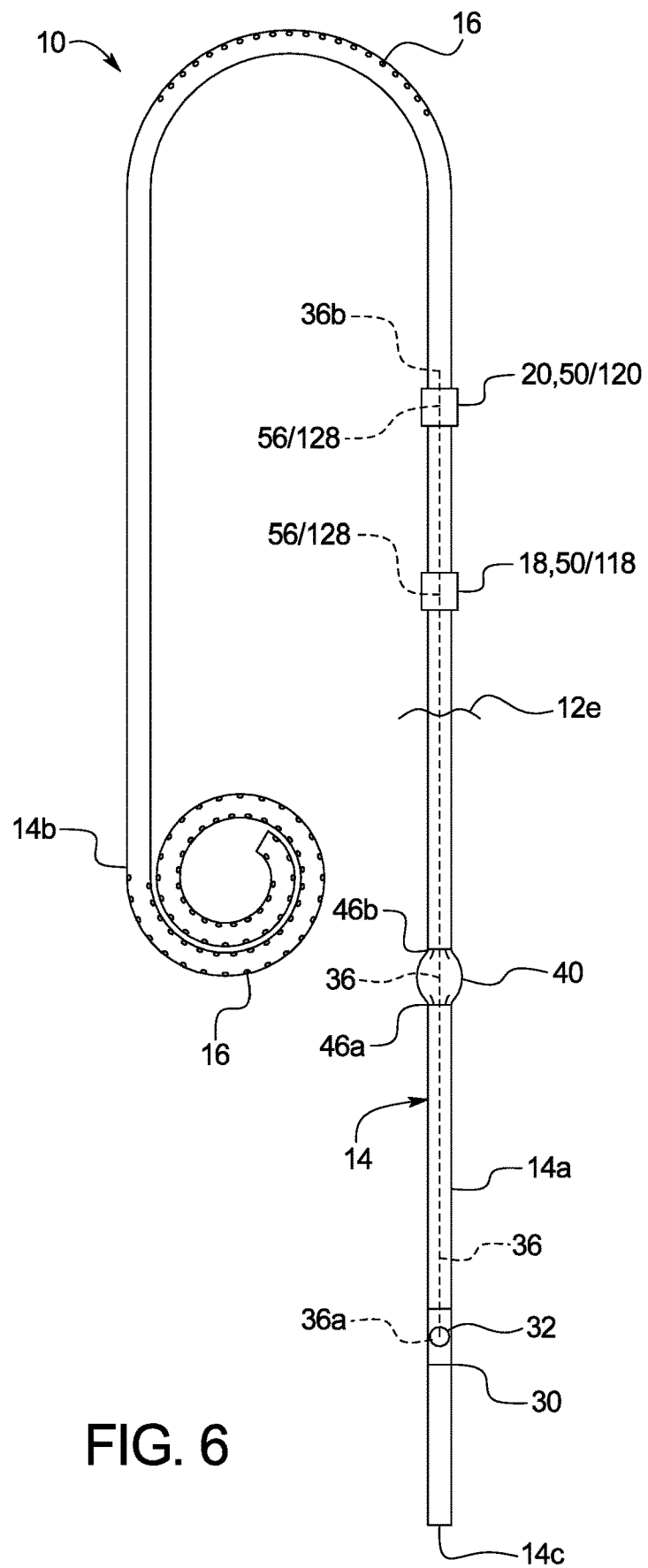
FIG. 6 is a top plan view of one embodiment of a drug diffusing catheter of the present disclosure illustrating a first alternative location for the antimicrobial agent reservoir.
Figure 7:
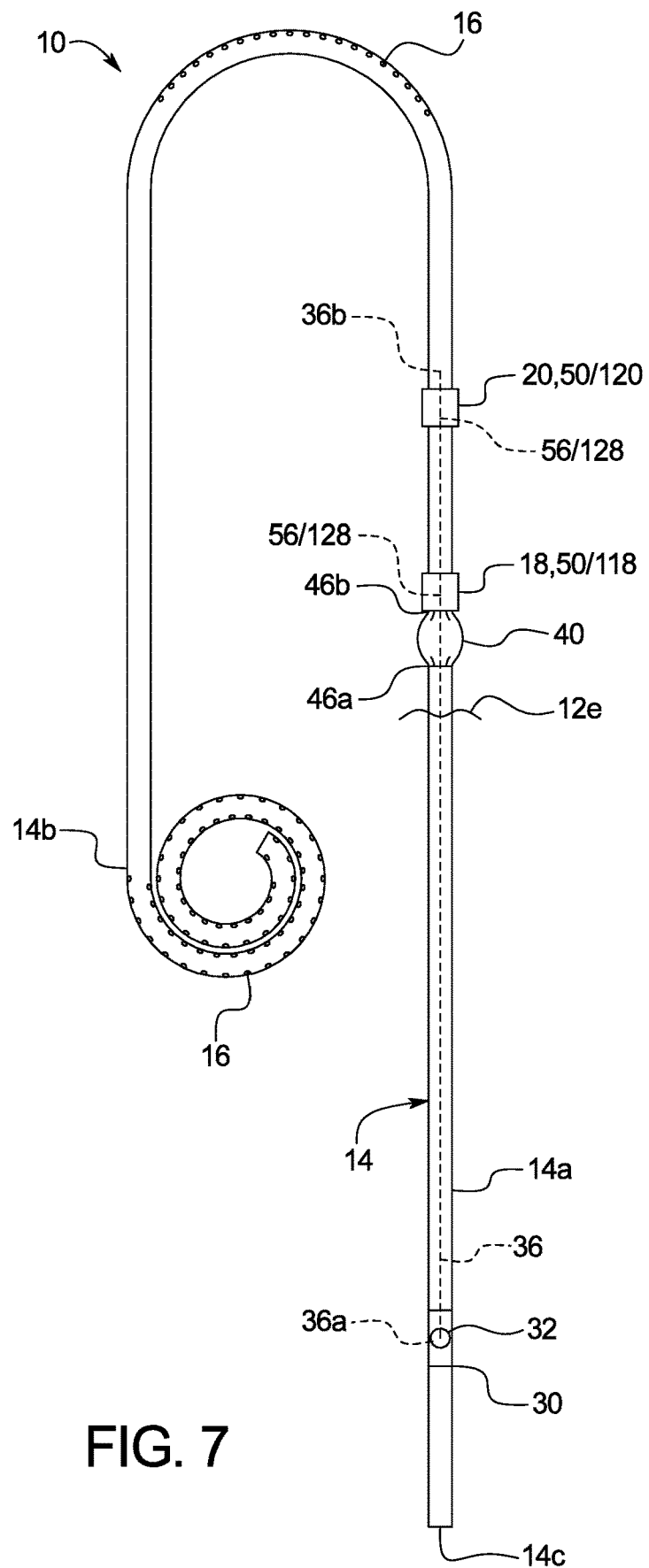
FIG. 7 is a top plan view of one embodiment of a drug diffusing catheter of the present disclosure illustrating a second alternative location for the antimicrobial agent reservoir.
Figure 8:
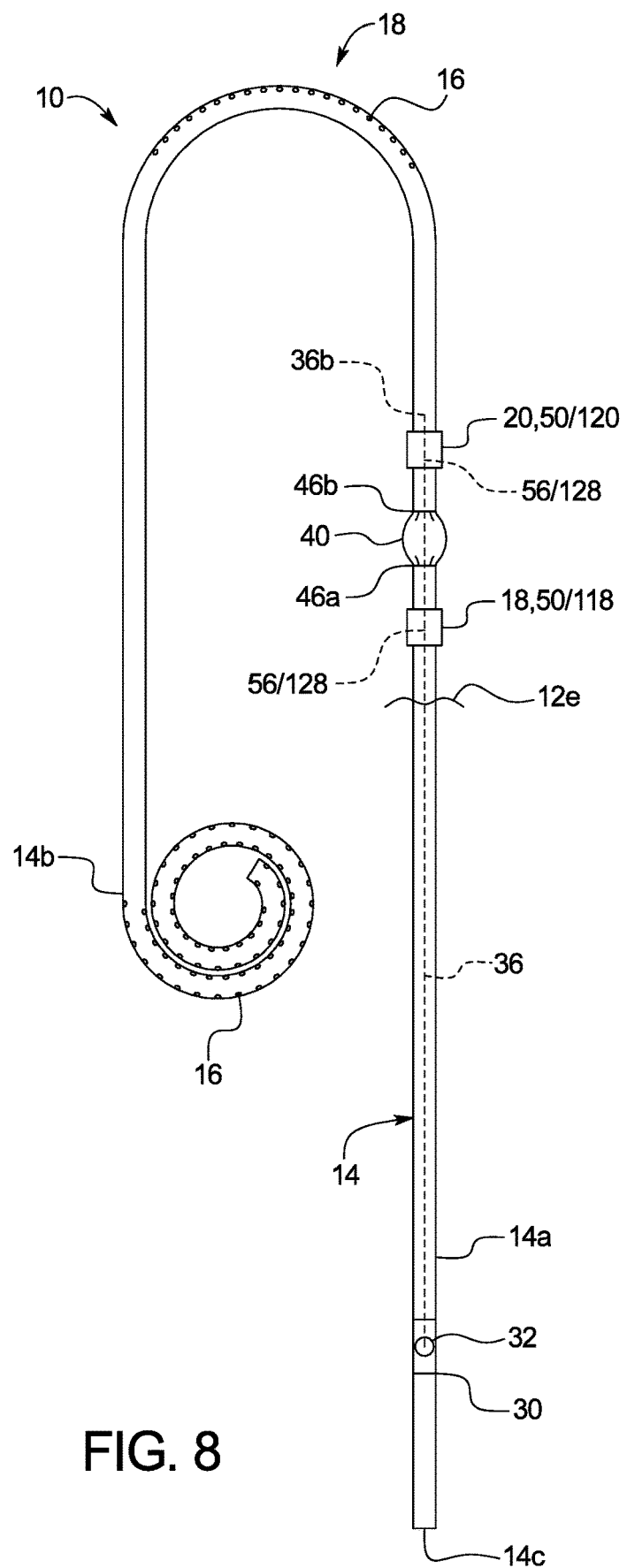
FIG. 8 is a top plan view of one embodiment of a drug diffusing catheter of the present disclosure illustrating a third alternative location for the antimicrobial agent reservoir.

FIG. 3A illustrates a first location for antimicrobial agent reservoir 40, which is located directly adjacent to or abutting access site 30. FIGS. 6 to 8 illustrate alternative locations for antimicrobial agent reservoir 40. FIGS. 6 to 8 illustrate drug diffusing catheter 10 having catheter tube 14, which beings at proximal tip 14c and extends from proximal end 14a to distal end 14b. Two sets of apertures or holes 16 are provided to disperse fresh dialysis fluid and retrieve used dialysis fluid from different locations within the patient's peritoneal cavity 12a. Proximal end 14a includes access site 30 having port 32 as described above. In FIGS. 6 to 8, delivery areas 50 are illustrated as being located with cuffs 18 and 20. Alternatively, integrated delivery area cuffs 118 and 120 are provided as described above. Delivery areas 50 are not restricted to cuffs 18 and 20 as discussed herein and may be located alternatively or additionally long catheter tube 14, such as exit site 12e.

FIGS. 6 to 8 further illustrate that flow path 36 begins at entrance end 36a located beneath port 32 of access site 30. Flow path 36 extends through antimicrobial agent reservoir 40 as illustrated in more detail in FIG. 3A. Flow path 36 extends further until reaching flow path 56/128 of first cuff and delivery area 18, 50/118. Flow path 36 extends from first flow path 56/128 to a second flow path 56/128 of second cuff and delivery area 20, 50/120. In the illustrated embodiment, flow path 36 extends slightly past second cuff and delivery area 20, 50/120 to distal end 36*b* to ensure that antimicrobial agent reaches all of second cuff and delivery area 20, 50/120.

As discussed above, it is contemplated that antimicrobial agent introduced by the operator into access site 30 will flow through and fill flow paths 36, 56/128. Once filled, further introduction of antimicrobial agent into access site 30 will pressurize the flow paths and force antimicrobial agent to, in no particular order, (i) fill reservoir 40 and (ii) squeeze antimicrobial agent through delivery areas 50 to the desired location along catheter tube 14, e.g., cuffs 18 and 20 (or into and through integrated delivery area cuffs 118 and 120 or exit site 12*e*).

FIG. 6 illustrates antimicrobial agent reservoir 40 located roughly half-way between access site 30 and first cuff and delivery area 18, 50/118 along catheter tube 14. In the illustrated embodiment, antimicrobial agent reservoir 40 is located proximal to patient exit site 12*e*. Reservoir 40 may be located alternatively anywhere between access site 30 and first cuff and delivery area 18, 50/118 along catheter tube 14.

FIG. 7 illustrates antimicrobial agent reservoir 40 located directly adjacent to or abutting first cuff and delivery area 18, 50/118. A wall of reservoir 40 may form a wall of first cuff and delivery area 18, 50/118 or vice versa. Antimicrobial agent reservoir 40 is located within patient 12, distal to patient exit site 12*e*. Here, reservoir 40 may but does not have to be of a variety in FIG. 3B or in which expandable layer 44 expands inwardly within lumen 22, so as not to disturb patient 12.

FIG. 8 illustrates antimicrobial agent reservoir 40 located roughly half-way between proximal cuff and delivery area 18, 50/118 and distal cuff and delivery area 20, 50/120. Antimicrobial agent reservoir 40 accordingly does not have to be upstream of delivery areas 50. Here, being located between the delivery areas (e.g., cuffs) may prove beneficial to allow time-delay release of antimicrobial agent to be most efficiently delivered to both delivery areas (e.g., cuffs). Again, antimicrobial agent reservoir 40 is located within patient 12, distal to patient exit site 12*e*, and may but does not have to be of a variety in FIG. 3B or in which expandable layer 44 expands inwardly within lumen 22, so as not to disturb patient 12.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis catheter comprising:
   a catheter tube sized to be inserted into a patient's peritoneal cavity, the catheter tube defining a lumen for carrying peritoneal dialysis fluid to at least one aperture located at or near a distal end of the lumen for delivery of the peritoneal dialysis fluid into the patient's peritoneal cavity;
   at least one cuff located along the catheter tube for attaching the catheter tube to the patient;
   an access site proximally spaced from the at least one cuff so as to remain external to the patient when the at least one cuff is attached to the patient, the access site allowing an antimicrobial agent to be introduced into the catheter tube;
   a reservoir in fluid communication with the access site, the reservoir configured to store an amount of the antimicrobial agent received from the access site for delivery after an antimicrobial agent introducer is removed from the access site; and
   a delivery area located distal or adjacent to and in fluid communication with the reservoir, the delivery area positioned so as to target delivery of the antimicrobial agent to the at least one cuff.

2. The peritoneal dialysis catheter of claim 1, wherein the at least one cuff includes first and second cuffs, wherein the delivery area of the catheter tube is a first delivery area positioned so as to target delivery of the antimicrobial agent to the first cuff, and which includes a second delivery area positioned so as to target delivery of the antimicrobial agent from the reservoir to the second cuff.

3. The peritoneal dialysis catheter of claim 2, wherein the reservoir is in antimicrobial agent flow communication with the first and second delivery areas.

4. The peritoneal dialysis catheter of claim 1, wherein the access site is configured to seal about the introducer, the introducer including a syringe or cannula.

5. The peritoneal dialysis catheter of claim 1, wherein the reservoir is an expandable reservoir.

6. The peritoneal dialysis catheter of claim 1, wherein the reservoir is disposed annularly about at least a portion of the lumen.

7. The peritoneal dialysis catheter of claim 1, wherein the delivery area is located distal to the reservoir, and wherein the catheter tube defines a flow path leading from the reservoir to the delivery area.

8. The peritoneal dialysis catheter of claim 1, wherein the delivery area includes first and second delivery areas, and wherein the reservoir is located proximal to the first and second delivery areas or between the first and second delivery areas.

9. The peritoneal dialysis catheter of claim 1, wherein the delivery area of the catheter tube is at least one of: configured to include minute flow paths leading to the at least one cuff, hydrophilic to the antimicrobial agent, or diffusive to the antimicrobial agent.

10. A peritoneal dialysis catheter comprising:
    a catheter tube sized to be inserted into a patient's peritoneal cavity, the catheter tube defining a lumen for carrying peritoneal dialysis fluid to at least one aperture located at or near a distal end of the lumen for delivery of the peritoneal dialysis fluid into the patient's peritoneal cavity;
    an access site located so as to remain external to the patient when the catheter tube is attached to the patient, the access site allowing an antimicrobial agent to be introduced into the catheter tube;
    a reservoir in fluid communication with the access site, the reservoir configured to store an amount of the antimicrobial agent received from the access site for delivery after an antimicrobial agent introducer is removed from the access site; and
    a delivery area located distal to the reservoir, wherein the delivery area is positioned so as to target delivery of the antimicrobial agent to a desired location along the catheter tube, and wherein the catheter tube defines a flow path for the antimicrobial agent, the flow path leading from the reservoir to the delivery area.

11. The peritoneal dialysis catheter of claim 10, wherein the desired location along the catheter tube includes at least one of (i) a cuff located along the outside of the catheter tube for attaching the catheter tube to the patient, (ii) an exit site of the catheter tube from the patient, or (iii) a subcutaneous area of the catheter tube.

12. The peritoneal dialysis catheter of claim 10, wherein the delivery area is integrated with a cuff for attaching the catheter tube to the patient.

13. The peritoneal dialysis catheter of claim 10, wherein the reservoir is an expandable reservoir.

14. The peritoneal dialysis catheter of claim 10, wherein the reservoir is disposed annularly about at least a portion of the lumen.

15. The peritoneal dialysis catheter of claim 10, wherein the delivery area includes first and second delivery areas, and wherein the reservoir is located proximal to the first and second delivery areas.

16. The peritoneal dialysis catheter of claim 10, wherein the delivery area of the catheter tube is at least one of: configured to include minute flow paths leading to at least one cuff, hydrophilic to the antimicrobial agent, or diffusive to the antimicrobial agent.

17. A peritoneal dialysis catheter comprising:
a catheter tube sized to be inserted into a patient's peritoneal cavity, the catheter tube defining a lumen for carrying peritoneal dialysis fluid to at least one aperture located at or near a distal end of the lumen for delivery of the peritoneal dialysis fluid into the patient's peritoneal cavity;
an access site located so as to remain external to the patient when the catheter tube is attached to the patient, the access site allowing an antimicrobial agent to be introduced into the catheter tube;
a reservoir in fluid communication with the access site, the reservoir configured to store an amount of the antimicrobial agent received from the access site for delivery after an antimicrobial agent introducer is removed from the access site;
a first delivery area located adjacent to and in fluid communication with the reservoir, wherein the first delivery area is positioned so as to target delivery of the antimicrobial agent to a first desired location along the catheter tube; and
a second delivery area located distal to and in fluid communication with the reservoir, wherein the second delivery area is positioned so as to target delivery of the antimicrobial agent to a second desired location along the catheter tube, and wherein the catheter tube defines a flow path between the first and second delivery areas.

18. The peritoneal dialysis catheter of claim 17, wherein the first and second desired locations along the catheter tube include at least one of (i) a cuff located along the outside of the catheter tube for attaching the catheter tube to the patient, (ii) an exit site of the catheter tube from the patient, or (iii) a subcutaneous area of the catheter tube.

19. The peritoneal dialysis catheter of claim 17, wherein the lumen additionally extends through the second delivery area.

20. A peritoneal dialysis catheter comprising:
a catheter tube sized to be inserted into a patient's peritoneal cavity, the catheter tube defining a lumen for carrying peritoneal dialysis fluid to at least one aperture located at or near a distal end of the lumen for delivery of the peritoneal dialysis fluid into the patient's peritoneal cavity;
an access site located so as to remain external to the patient when the catheter tube is attached to the patient, the access site allowing an antimicrobial agent to be introduced into the catheter tube;
a reservoir in fluid communication with the access site, the reservoir configured to store an amount of the antimicrobial agent received from the access site for delivery after an antimicrobial agent introducer is removed from the access site;
a first delivery area located distal to and in fluid communication with the reservoir, wherein the first delivery area is positioned so as to target delivery of the antimicrobial agent to a first desired location along the catheter tube; and
a second delivery area located distal to the first delivery area and in fluid communication with the reservoir, wherein the second delivery area is positioned so as to target delivery of the antimicrobial agent to a second desired location along the catheter tube, and wherein the catheter tube defines a first flow path between the reservoir and the first delivery area and a second flow path between the first and second delivery areas.

* * * * *